Figure 1:
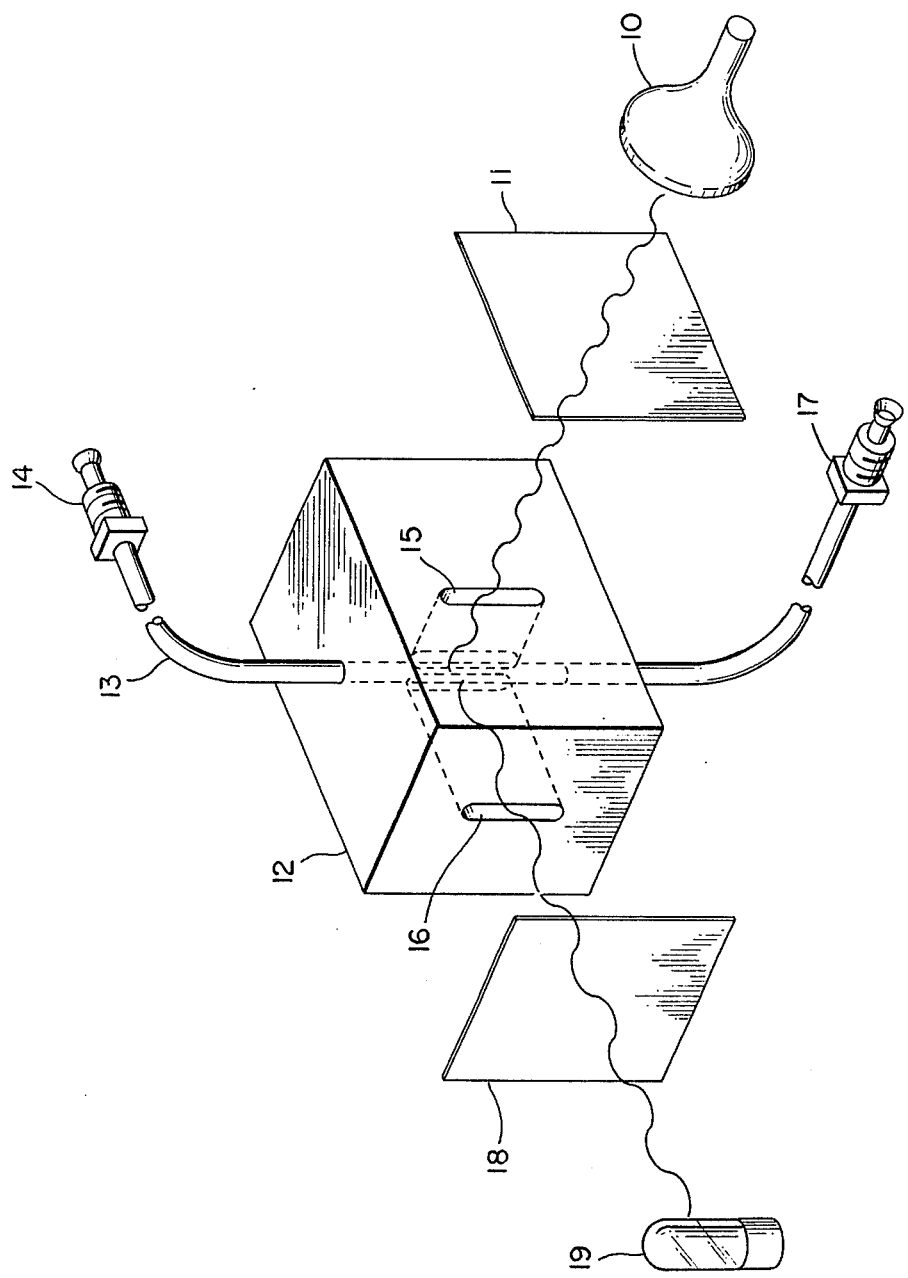

United States Patent [19]

Zdrodowski

[11] 4,008,397
[45] Feb. 15, 1977

[54] FLUOROMETER FLOW CELL

[75] Inventor: Joseph John Zdrodowski, Bricktown, N.J.

[73] Assignee: Hoffmann-La Roche Inc., Nutley, N.J.

[22] Filed: Apr. 24, 1975

[21] Appl. No.: 571,147

[52] U.S. Cl. .............................. 250/373; 250/461 R; 356/85
[51] Int. Cl.² ..................... G01J 1/42; G01N 21/38
[58] Field of Search ............... 250/373, 461 B, 301, 250/302, 373, 461; 356/85

[56] References Cited

UNITED STATES PATENTS

| 3,413,464 | 11/1968 | Kamentsky | 250/461 B |
| 3,586,859 | 6/1971 | Katz et al. | 250/461 |
| 3,917,404 | 11/1975 | Heiss | 356/85 |

Primary Examiner—Archie R. Borchelt
Attorney, Agent, or Firm—Samuel L. Welt; George M. Gould

[57] ABSTRACT

An improved fluorometer flow cell is described wherein the flow cell is constructed entirely of a light transparent polyfluoroethylene tubing.

4 Claims, 1 Drawing Figure

FLUOROMETER FLOW CELL

BACKGROUND OF THE INVENTION

Flow cells utilized in fluorometers have up till now been constructed out of quartz. Such cells require complicated fittings and seals which were costly and prone to leak. It has not been believed possible to substitute plastic materials for the quartz cells known in the art as it was believed that such plastic materials would be fluorescent in the desired ultraviolet region utilized in the fluorometer and thus would interfere with the measurement of the fluorescence of the sample passing through the flow cell.

DESCRIPTION OF THE INVENTION

The present invention relates to an improved fluorometer flow cell which is constructed entirely of a clear plastic tubing. Such improved fluorometer flow cell has the advantages of being far less expensive to construct than the quartz flow cells of the prior art and further can be adapted to take conventional fittings thus allowing direct connection to an inlet source in a leak proof fashion. A further feature of the present invention is that the tubing utilized can be selected to maintain the same inside diameter as the inlet source system. This will eliminate diffusion and turbulence in the flow cell providing sharper and more symmetrical peaks during the analysis.

The preferred plastic material utilized in the practice of the present invention is polyfluoroethylene, i.e., Teflon, a trademark of E. I. DuPont de Nemours & Co. Most preferably the Teflon used will be of optical grade and thus essentially transparent to ultraviolet radiation. It has unexpectedly been found that Teflon tubing does not fluoresce in the UV at wave lengths above 300 nm. It is thus possible to employ the Teflon fluorometer flow cell in conjunction with fluorogens derived from fluorescamine (Fluram, a trademark of Hoffmann-La Roche Inc.). Thus, for example, the improved fluorometer of the present invention may be utilized as part of an automatic fluorescent detection system such as described for example in U.S. Pat. No. 3,876,881 issued Apr. 8, 1975.

The fluorometer of the present invention will be more clearly understood by reference to the Drawing. Light from a conventional light source 10 such as a xenon or a xenon-mercury lamp, which are employed in fluorometers known in the art, is passed through filter means 11 so as to provide a radiation source of desired wave length to serve in the excitation of the fluorogen contained in the fluorometer flow cell. Such flow cell 13 as indicated is preferably constructed of optical grade Teflon and is adapted with fittings 14 and 17 to allow leakproof fluid connections with a desired inlet and outlet source respectively. As indicated above the internal diameter of this tubing can be selected to be identical with that of the inlet system to avoid undesired diffusion and turbulence effects.

The tubing is passed through a cell holder means 12 by appropriate apertures contained therein. Thus in a preferred embodiment cell holder 12 can be conveniently prepared from a black anodized aluminum block.

The excitation radiation beam enters the cell holder by means of aperture 15 which allows said radiation beam to strike upon the tube 13. Such excitation radiation will generally be at a wave length of about 390 to 395 nm. when employing fluorescamine as the fluorogenic reagent.

If a fluorescent material is present in the flow cell, the fluorescent radiation will be emitted from tubing 13 and is passed through aperture 16 out of the cell holder. Aperture 16 is drilled in cell holder 12 at an angle of 90° from aperture 15. Filter means 18 is provided to allow cutoff of all undesired radiation below the emission wave lengths and the resulting radiation beam is then passed to photodetection means 19 to be measured in conventional manner.

I claim:
1. In a fluorometer consisting of
   A. light source means;
   B. excitation filter means;
   C. cell holder means;
   D. emission filter means; and,
   E. photo detector means,
the improvement which comprises providing said cell holder means with a flow cell consisting of polyfluoroethylene tubing which is in operative optical relationship with said light source, said excitation filter means, said emission filter means and said detector means.

2. The fluorometer of claim 1 wherein said polyfluoroethylene is of optical grade.

3. The fluorometer of claim 1 wherein said polyfluoroethylene tubing has fittings at a first end to provide direct leakproof connection with an inlet source and has fittings at a second end to provide direct leakproof connection with an outlet source.

4. The fluorometer of claim 3 wherein the inner diameter of said polyfluoroethylene tubing is the same as that of said inlet source.

* * * * *